United States Patent [19]

Daniel et al.

[11] Patent Number: 5,696,193
[45] Date of Patent: Dec. 9, 1997

[54] IMMUNOASSAY ELEMENTS COMPRISING POLYMERS CONTAINING VANDIUM IV (V+4) IONS

[75] Inventors: Daniel Salman Daniel, Rochester; David Alan Hilborn, Henrietta; Calvin Roman Messing, Spencerport; Ignazio Salvatore Ponticello, Pittsford; Susan Jean Danielson, Rochester, all of N.Y.

[73] Assignee: Clinical Diagnostic Systems, Inc., Rochester, N.Y.

[21] Appl. No.: 232,920

[22] Filed: Apr. 25, 1994

[51] Int. Cl.[6] .................. G01N 33/53; C08F 8/00; C08F 8/12; C08F 8/42
[52] U.S. Cl. .................. 524/408; 525/326.6; 525/326.7; 525/328.2; 525/328.4; 525/328.5; 525/328.6; 525/328.8; 525/328.9; 525/329.4; 525/329.5; 525/329.7; 525/329.8; 525/330.1; 525/330.2; 525/330.3; 525/330.4; 525/330.6; 525/343; 525/344; 525/346; 525/353; 525/354; 525/360; 525/196; 525/326.8; 525/326.9; 525/329.2
[58] Field of Search ............ 524/408; 525/326.6, 525/196, 326.7, 326.8, 328.2, 326.9, 328.4, 329.2, 328.5, 328.6, 328.8, 328.9, 329.4, 329.5, 329.7, 329.8, 330.1, 330.2, 330.3, 330.4, 330.6, 343, 344, 346, 353, 354, 360

[56] References Cited

U.S. PATENT DOCUMENTS

| | | | |
|---|---|---|---|
| 3,950,313 | 4/1976 | Bain et al. | 260/79.5 C |
| 4,228,240 | 10/1980 | Dawson et al. | 435/188 |
| 4,346,231 | 8/1982 | Ponticello et al. | 560/178 |
| 5,516,645 | 5/1996 | Daniel et al. | 435/7.92 |

OTHER PUBLICATIONS

"Polymer–Anchored Vanadyl Catalysts for the Oxidation of Cyclohexene", Linden et al., Journal of Catalysis, vol. 48, pp. 284–291.

*Primary Examiner*—Frederick Krass
*Attorney, Agent, or Firm*—Dana M. Schmidt

[57] ABSTRACT

A dry immunoassay analytical element, for assaying a ligand, comprising in the following order:

(a) a layer containing a labeled ligand;
(b) a spreading layer;
(c) a receptor layer containing a fixed concentration of an immobilized receptor for the labeled ligand and the receptor is i) covalently bonded to polymeric beads having a diameter in the range of 0.1 to 5 μm and ii) dispersed in a polymeric binder and
(d) a support;

characterized in that the spreading layer contains a water soluble polymer containing vanadium IV ($V^{+4}$) ions.

5 Claims, No Drawings

IMMUNOASSAY ELEMENTS COMPRISING POLYMERS CONTAINING VANDIUM IV (V+4) IONS

RELATED CASES

The present case is related to U.S. patent application Ser. No. 08/232,903, filed on the same date as the present application in the name Daniel S. Daniel, et al and entitled IMMUNOASSAY ANALYTICAL ELEMENTS CONTAINING VANADIUM IV ($V^{+4}$) IONS and now U.S. Pat. No. 5,516,645.

FIELD OF THE INVENTION

This invention relates to an immunoassay element and use thereof in an immunoassay.

BACKGROUND OF THE INVENTION

Immunoassays, which take advantage of natural immunological reactions, have found wide-spread use as analytical techniques in clinical chemistry. Because of the specificity of the reactions, they are particularly advantageous in quantifying biological analytes that are present in very low concentration in biological fluids. Such analytes include, for example, antigens, antibodies, therapeutic drugs, narcotics, enzymes, hormones, proteins, etc.

The analyte, which is the target of the assay is referred to herein as the ligand, and the labeled analyte is referred to as the labeled ligand (including immunocompetent derivatives and analogs of such ligand). Compounds which specifically recognize the ligand and the labeled ligand and react to form complexes with them are referred to herein as receptors. The receptor and the ligand or labeled ligand form a conjugate pair. Any member of the pair can function as a receptor or a ligand.

In competitive binding immunoassays, a labeled ligand is placed in competition with unlabeled ligand for reaction with a fixed amount of the appropriate receptor. Unknown concentrations of the ligand can be determined from the measured signal of either the bound or unbound (i.e. free) labeled ligand. The reaction proceeds as follows:

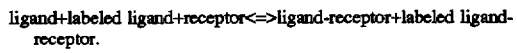

ligand+labeled ligand+receptor<=>ligand-receptor+labeled ligand-receptor.

Immunoassay analytical elements are known. In general, such elements comprise receptors, such as antibodies for a ligand, immobilized in a particulate layer. In addition the element usually contains a reagent system that, through interaction with a bound or unbound species, results in a signal that can be correlated to the concentration of ligand in a sample. In use, the sample is manually combined with an enzyme labeled ligand and applied to the element. After a time, a solution containing a substrate for the labeled ligand is applied to the particulate layer. The reaction with the substrate is catalyzed by the enzyme label to form a reaction product that ultimately causes a signal color to develop. The reflection density of the color can be correlated to the concentration of the ligand in the sample. Similar signal development systems are known for other known conventional labels such as radioactive tags, chromophores, fluorophores, stable free radicals, and enzyme cofactors, inhibitors and allosteric effectors.

Multilayer immunoassay elements are thin film elements which use the above described immunoassay principles to measure analytes in serum samples. In these elements, the rate of color formation is inversely correlated to the amount of analyte present. Also, the rate of color formation is directly proportional to the activity of the drug-labeled enzyme bound to the immobilized antibody. For the immunoassays to maintain a stable calibration, none of the enzyme activity (measured rate) can be lost in any of the slides during the specified calibration period.

Frequently, immunoassay elements are supplied to customers in plastic "cartridges" containing 50 separate elements from which one element may be removed at a time as needed. The elements are stacked one on top of another so that the lower 49 elements in the cartridge all have their top surfaces covered by the element above. However, the top element in the stack has no such covering, and therefore the surface of that element is exposed to environmental factors to which the other 49 elements are not. For example, the top (or first) element is more exposed to air flow and light than the remainder of the elements when the cartridges are being handled during manufacturing or when the cartridges are in the element supplies of the clinical analyzers.

During storage, prior to use, the cartridges themselves are stored in sealed, foil-lined bags. However, the top element is still more exposed to the residual air and humidity inside the sealed bags than the other 49 elements.

It has been found that, when a common test fluid was reacted with the elements in a cartridge, the rate of color formation observed in the top (or first) element was always lower than the rate of color formation observed when the same test fluid was applied to elements below the top element in the same cartridge.

SUMMARY OF THE INVENTION

The objective of the present invention is to substantially eliminate the lower rate of color formation of the first element in the top element of the cartridge.

DETAILS OF THE INVENTION

The elements of this invention comprise labeled ligand, spreading and receptor zones. The various zones can be in one coated layer or in separate coated layers. For example the spreading zone and the receptor zone can be in a single layer or they can be in separate layers. The separate layers can be arranged in any order on the support. Or the separate layers can be arranged such that the receptor layer is directly on the support, the spreading layer directly above the receptor layer and the labeled ligand zone over the spreading layer. When the receptor zone forms an entirely separate layer, the layer will also include a binder of the type describe hereinafter. The element can include additional layers such as those described infra. All of such layers can be coated using coating techniques known in this art and which are briefly described infra.

The labeled ligand zone or layer may be gravure coated to 1) minimize wet coverage of the labeled ligand coating composition, to avoid precontact of the labeled ligand with the receptor, while at the same time maintaining enough wetness to achieve uniform coverage of the labeled ligand, and 2) achieve rapid drying in a way that a) removes substantially all of the coating solvent; b) avoids adversely affecting the porosity of the spread layer and spreading time, and c) maintains sufficient enzyme activity.

The relative affinity of antibody and labeled ligand for each other is also an important factor in minimizing prebinding. This factor is controlled, as is well known by those skilled in this art, by manipulating the structure of the labeled ligand together with a prudent choice of antibody.

In general the level of coated labeled ligand coverage needed in an element is determined empirically for each specific immunoassay according to the following procedure:

1. Determine the concentration of labeled ligand needed to achieve acceptable immunoassay performance when the immunoassay is performed by contacting the analytical element with the labeled ligand concurrently with a sample. Acceptable assay performance is achieved when (a) the assay can be carried out in less than 20 minutes; (b) the dynamic range of the assay is such that the minimum and maximum ligand concentrations detectable cover a clinically useful concentration range; and (c) clinically significant ligand concentrations can be detected across the dynamic range.

2. Empirically determine the level of coated labeled ligand coverage needed with the same analytical element to achieve the above established acceptable assay performance by:

A. Coating, directly over the particulate receptor zone of the element used to establish optimum spotted labeled ligand levels, the labeled ligand at a coverage in g/m$^2$ that is some fraction, multiple or the same as the concentration of labeled ligand used in spotting the labeled ligand in 1, supra.

B. Conduct a series of assays with test samples containing a known concentration of the ligand.

C. Compare the results of the assays with the known concentration of ligand; and D. Repeat steps B and C as needed, varying the labeled ligand coverage according to the results seen in step 2C to determine the labeled ligand coverage required.

Depending on the labeled ligand, the coverage of the labeled ligand could be less than, the same as or several multiples greater (2×, 3×, 4×, etc.) than the labeled ligand concentration needed when the same assay is carried out by spotting the labeled ligand directly on the analytical element.

Using the above guidelines, carefully controlled gravure coating procedures were successfully carried out using the following coverages and drying protocols. The labeled ligand coatings in the elements of the invention were prepared with a gravure machine (made by Yasui of Japan). Drying conditions used for all of the examples were 120° F. (49° C.) in the first drying section only. The second section was not used. The gravure cylinder used contained 295 cells/inch (1.344×10$^8$ cells/m$^2$). The cells had a depth of 19 microns, a width of 72 microns and a land width between cells of 12 microns. This cylinder will deliver about 4.3 g/m$^2$ of coating composition containing the labeled ligand to the bead spreading zone using the direct gravure process at a coating machine speed of 50 ft/min (15.24 m/minute). Those skilled in the gravure coating arts will be readily able to adapt the previously described procedure to any gravure coating machine. The coating composition for the labeled ligand was as follows:

Coated Labeled Ligand Coating Composition
Based on 4.3 g/m$^2$ Wet Coverage

| Component | g/m$^2$ Dry Coverage |
|---|---|
| MOPS Buffer | .0045 |
| BSA (Bovine Serum Albumin) | .000215 |
| poly (acrylamide) | .00108 |
| 4'-Hydroxyacetanilide | .000325 |
| *Labeled ligand | .000016 |

*Labeled ligand has been coated anywhere between 4 and 64 μg/m$^2$

The remaining layers of the element can be coated using well known coating techniques in this art. To minimize prebinding it is recommended that each separate layer or zone be coated separately and allowed to dry before application of subsequent layers or zones.

The spreading zone, when coated as a separate layer, is porous and coated over the receptor layer. It contains, as an essential ingredient a water soluble polymer containing recurring polymerized monomers having vanadium IV ions to form a salt or a liganded metal complex. The ion may be present as vanadyl (VO$^+$2) ions. The polymer generally is selected from a) polymer salts having recurring anionic monomers containing vanadyl (VO$^+$2) and b) polymers having heteroatoms that have formed ligands with vanadyl (VO$^+$2) ions Monomers containing anionic groups such as sulfonate, sulfate, carboxylate, phosphate and phosphonate are used to form the polymer salts used in the invention. Monomers containing heteroatom ligand complexing groups such as β-diketone, amine, sulfhydryl, carbonyl, carboxy and hydroxy are used to form the polymer ligand complexes.

Useful water soluble polymer salts and polymer ligand complexes are formed with polymers having the structure (I):

(A)$_x$ (B)$_y$ (C)$_z$;

wherein

A represents polymerized hydrophilic monomers selected from the group consisting of acrylamide, N-isopropylacrylamide, N-t-butylacrylamide, 1-vinylimidazole, N-vinylpyrrolidone, N-methylolacrylamide, 2-hydroxyethyl acrylate, and 2,3-dihydroxypropyl acrylate;

B represents polymerized monomers selected from monomers containing an anionic or metal complexing or ligand forming group selected from the group consisting of sulfonate; sulfate; carboxylate; phosphonate; phosphate; β-diketone

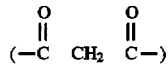

groups; primary, secondary, or tertiary amine groups; carboxyl; carbonyl; and hydroxy groups;

C represents recurring units derived from any other monomers which are compatible with the immunoassay analytical element x is 20 to 98 weight percent;

y is 2 to 80 weight percent; and z is 0 to 20 weight percent.

Monomers within the above definition of B- include N-(3-acetoacetamidopropyl)methacrylamide, 2-acetoacetoxyethyl methacrylate, N-(2-acetoacetoxyethyl) acrylamide, N-(2-acetoacetamidoethyl)methacrylamide, sodium 2-acrylamido-2-methylpropanesulfonate, sodium 3-acryloyloxypropane-1-sulfonate, 2-aminoethyl methacrylate hydrochloride, N-(3-aminopropyl)methacrylamide hydrochloride, acrylic acid, methacrylic acid, 3-(p-vinylbenzylthio)propionic acid, 2-phosphatoethyl acrylate, 2-phosphatoethyl methacrylate, 3-phosphatopropyl acrylate, 3-phosphatopropyl methacrylate, 2-sulfatoethyl methacrylate, and N-(m-&p-vinylbenzyl)nitrilodiacetic acid.

The amine group-containing monomers are typically incorporated as the amine acid addition salt (—NH$_2$.HX and X is an acid anion). The copolymer can contain a mixture of different anionic and heteroion group-containing monomers within the above definitions. However the polymer must be water soluble.

The β-diketone monomers and polymers containing them are disclosed in Eastman Kodak Company U.S. Pat. Nos. 3,459,790, 3,488,708, 2,865,893, 2,860,986, 2,904,539, 3,554,987, 3,658,878, 3,929,482, 3,939,130, 4,346,231, 4,438,278, 4,421,915, and 3,904,418. Preferred monomers are those of U.S. Pat. No. 4,438,278.

The polymers used in the present invention are preparedly simply mixing, at room temperature, an aqueous solution of the polymer (typically the polymer reaction mixture at about 5 to 25% solids) with a salt or a solution of a salt of the metal ion (about 20–100% solution), preferably a vanadyl sulfate salt or salt solution, in a ratio of metal salt to complexing groups (i.e., monomer B when B has one complexing group such as one anionic, amine, or β-diketone group) of from about 0.1/1 up to about 1/1, preferably about 1/1.

Other materials for use in spreading layers are well known in the art of making dry analytical elements as disclosed, for example, in U.S. Pat. No. 4,258,001. Such layers include macroporous layers made from cloth, paper, etc. A preferred particulate layer is a bead spreading layer (BSL). This layer can be easily constructed to have suitable porosity for use in the elements of the present invention to accommodate a test sample (e.g. 1 to 100 mL), diluted or undiluted. Preferably, the spreading layer is isotropically porous, which property is created by interconnected spaces between the particles comprising the zone. By isotropically porous is meant that the spreading layer uniformly spreads the applied fluid in all directions throughout the layer.

Useful spreading layers, including bead spreading layers are disclosed in U.S. Pat. Nos. 4,670,381; 4,258,001 and 4,430,436. Particularly useful spreading layers are those having a particulate structure formed by organo-polymeric particles and a polymeric adhesive for those particles described in U.S. Pat. No. 4,258,001. The organo-polymeric particles useful in the spreading layer are generally heat-stable, spherical beads having a particle size in the range of from about 10 to 40 µm in diameter or even smaller.

The particles can be composed of a wide variety of organic polymers, including both natural and synthetic polymers, having the requisite properties. Preferably, however, they are composed of one or more addition polymers described in the aforementioned patents.

When the receptor zone is coated as a separate layer it is prepared and coated over a support. The receptors are covalently bonded to polymer particles through surface reactive groups on the receptor (nucleophilic free amino groups and sulfhydryl groups).

A general procedure for attaching receptors to the small polymer beads includes covalently attaching the selected receptor to the beads using generally known reactions. With many pendant groups for example the haloalkyl, 2-substituted activated ethylsulfonyl and vinylsulfonyl, the receptor can be directly attached to the beads. Generally, the beads are mixed with the receptor in an aqueous buffered solution (pH generally from about 5 to about 10) and a concentration of from about 0.1 to about 40 weight percent polymer particles (preferably from about 0.1 to about 10 weight percent). The amount of receptor is at a ratio to polymer of from about 0.1:1000 to about 1:10, and preferably from about 1:100 to about 1:10. Mixing is carried out at a temperature in the range of from about 5° to about 50° C., and preferably at from about 5° to about 40° C., for from about 0.5 to about 48 hours. Any suitable buffer can be used.

In some instances, the pendant reactive groups on the outer surface must be modified or activated in order to cause covalent attachment of the ligand. For example, carboxyl groups must be activated using known carbodiimide or carbamoylonium chemistry, described in EP 308235 published 22 Jul. 1992 and U.S. Pat. No. 5,155,166.

The attachment of the receptor to carboxyl group-containing monodispersed polymer beads, however, is carried out in two steps, the first of which involves contacting an aqueous suspension of the particles with a carbodiimide or a carbamoylonium compound to produce reactive intermediate polymer particles having intermediate reactive groups in place of the carboxyl groups. This step is carried out at a suitable pH using suitable acids or buffers to provide the desired pH. Generally, the pH is less than 6, but this is not critical as long as the reaction can proceed. More likely, the pH is between about 3.5 and about 7. The molar ratio of carbodiimide or carbamoylonium compound to the carboxyl groups on the surface of the particles is from about 10:1 to 500:1.

In the second step of the method, the reactive intermediate formed in the first step is contacted with a reactive amine- or sulfhydryl-group containing receptor. A covalent linkage is thereby formed between the particles and the receptor. The weight ratio of the receptor to the polymeric particles is generally from about 1:1000 to about 1:1, and preferably from about 1:100 to about 1:10.

In other instances, an epoxy group on the outer surface can be hydrolyzed to form a diol compound capable of reacting with cyanogen bromide which can act as a coupling agent for amine groups in the immunological species. Aldehydes can react directly with amines to form a Schiff's base which can be subsequently reduced to form a covalent link. Alternatively, the aldehyde can be oxidized to an acid and chemistry identified above for carboxyl groups can be used to form an amide linkage.

Any reactive amine- or sulfhydryl-containing receptor can be attached to the monodispersed polymeric beads as long as that receptor contains a reactive amine or sulfhydryl group, respectively which will react with the reactive groups on the polymer or with the intermediate formed by the reaction of a carbodiimide or a carbamoylonium compound with carboxyl groups on the particles in the case which the polymer has reactive carboxyl groups.

The small polymer beads having reactive groups that readily react directly with the amine or sulfhydryl groups on the receptors are simply mixed with the receptors, in an appropriate buffer if necessary, and allowed to react.

Polymers from which beads for the receptor can be selected include the following: poly(m & p-chloromethylstyrene), poly(styrene-co-m & p-chloromethylstyrene-co-2-hydroxyethyl acrylate) (67:30:3 molar ratio), poly(styrene-co-m & p-chloroethylsulfonylmethylstyrene) (95.5:4.5 molar ratio), poly{styrene-co-N-[p-(2-chloroethylsulfonylmethyl) phenyl]acrylamide} (99.3:0.7 molar ratio), poly(m & p-chloromethylstyrene-co-methacrylic acid)(95:5, 98:2 and 99.8:0.2 molar ratio), poly(styrene-co-m & p-chloroethylsulfonylmethylstyrene-co-methacrylic acid) (93.5:4.5:2 molar ratio), poly{styrene-co-N-[p-(2-chloroethylsulfonylmethyl)phenyl]acrylamide-co-methacrylic acid} (97.3:0.7:2 molar ratio), poly(styrene-co-m & p-chloromethylstyrene) (70:30 molar ratio), poly [styrene-co-3-(p-vinylbenzylthio)propionic acid] (97.6/2.4 molar ratio), poly(styrene-co-vinylbenzyl chloride-co-acrylic acid) (85:10:5 molar ratio), poly(styrene-co-acrylic acid) (99:1 molar ratio), poly(styrene-co-methacrylic acid) (90:10 molar ratio), poly(styrene-co-acrylic acid-co-m & p-divinylbenzene) (89:10:1 molar ratio), poly(styrene-co-2-carboxyethyl acrylate) (90:10 molar ratio), poly(methyl methacrylate-co-acrylic acid) (70:30 molar ratio), poly (styrene-co-m & p-vinylbenzaldehyde)(95:5 molar ratio), and poly(styrene-co-m & p-vinylbenzaldehyde-co-methacrylic acid)(93:5:2 molar ratio).

The element is carried on a suitable support. The receptor layer is coated over the support although there may be intervening layers, such as a gelatin/buffer layer, between the support and the receptor layer. The support can be any suitable dimensionally stable, and preferably, nonporous and transparent (i.e. radiation transmissive) material which transmits electromagnetic radiation of a wavelength between about 200 and about 900 nm. A support of choice for a particular element should be compatible with the intended mode of detection (reflection, transmission or fluorescence spectroscopy). Useful support materials include polystyrene, polyesters [e.g. poly(ethylene terephthalate)], polycarbonates, cellulose esters (e.g. cellulose acetate), etc.

Polymeric binders for the receptor layer are described generally in Canadian patent 1,240,445 and are expressly incorporated herein by reference. Useful polymers are chill-gellable polymers comprising from about 30 to 97 weight percent of polymerized N-alkyl substituted acrylamide such as N-isopropylacrylamide. Other useful N-alkyl-substituted acrylamides include N-n-butylacrylamide, N,N-diethylacrylamide and N-n-propylacrylamide. Poly(N-isopropylacrylamide-co-methacrylic acid-co-N,N'-methylenebisacrylamide) is used in the examples to illustrate the utility of these binders.

The polymer binder also comprises from about 3 to 25 weight percent of one or more polymerized crosslinking monomers having at least two addition-polymerizable groups per molecule. These crosslinking monomers are generally well known in the art. The preferred crosslinking monomers contain acrylamido or methacrylamido groups to facilitate polymerization with the N-alkyl-substituted acrylamides.

Examples of useful crosslinking monomers include:
N,N'-methylenebisacrylamide;
N,N'-methylenebismethacrylamide;
ethylene dimethacrylate;
2,2-dimethyl-1,3-propylene diacrylate;
divinylbenzene;
mono[2,3-bis(methacryloyloxy)propyl]phosphate;
N,N'-bis(methacryloyl)urea;
triallyl cyanurate;
allyl acrylate;
allyl methacrylate;
N-allylmethacrylamide;
4,4'-isopropylidenediphenylene diacrylate;
1,3-butylene diacrylate;
1,4-cyclohexylenedimethylene dimethacrylate;
2,2'-oxydiethylene dimethacrylate;
divinyloxymethane;
ethylene diacrylate;
ethylidene diacrylate;
propylidene dimethacrylate;
1,6-diacrylamidohexane;
1,6-hexamethylene diacrylate;
1,6-hexamethylene dimethacrylate;
phenylethylene dimethacrylate;
tetramethylene dimethacrylate;
2,2,2-trichloroethylidene dimethacrylate;
ethylenebis(oxyethylene) diacrylate;
ethylenebis(oxyethylene) dimethacrylate;
ethylidyne trimethacrylate;
propylidyne triacrylate;
vinyl allyloxyacetate;
1-vinyloxy-2-allyloxyethane;
2-crotonoyloxyethyl methacrylate;
diallyl phthalate; and
2-(5-phenyl-2,4-pentadienoyloxy)ethyl methacrylate.

These chill gellable polymeric binders can also include 0 to 60 weight percent of polymerized hydrophilic monomers. Amounts of 5 to 35 weight percent are also useful. Hydrophilic monomers are disclosed in Canadian patent 1,240,445. In particular such monomers have one or more groups selected from hydroxy, pyrrolidone, amine, amide, carboxy, sulfo, carboxylate salt, sulfonate salt and sulfate salt groups. Generally the counter ions of the salt groups are alkali metal or ammonium. Useful hydrophilic monomers are acrylic acid and methacrylic acid and their salts, 2-acrylamido-2-methylpropane sulfonate, 2-hydroxyethyl acrylate, 2-hydroxyethyl methacrylate, 2-hydroxypropyl acrylate, 2-hydroxypropyl methacrylate and glyceryl methacrylate.

Further, the recited binders make it possible to form uniform coatings of receptor layers due to the very low binder viscosities achieved from sheer thinning during extrusion hopper coating. A further advantage is achieved with the recited binders in that, immediately after forming uniform coatings, the viscosity of the binders increases substantially resulting in a "set layer" that remains stable and uniform during wet transport and drying of the binders.

The receptors can also be dispersed in a polymer binder selected from the group consisting of:
poly(vinyl alcohol);
bovine serum albumin;
acacia gum;
homopolymers of poly-N-vinylpyrrolidone having a molecular weight in the range 8000 to 400,000; and
water-soluble vinyl addition copolymers having two or more monomers selected from the group consisting of acrylamide, methacrylamide, N-alkyl-substituted acrylamides, N-alkyl substituted methacrylamides, 1-vinylimidazole, 2-alkyl substituted-1-vinylimidazoles, 2-hydroxyalkyl substituted-1-vinylimidazoles, N-vinylpyrrolidone, hydroxyalkyl acrylates, hydroxyalkyl methacrylates, acrylic acid, and methacrylic acid; wherein alkyl and hydroxyalkyl in the copolymers has 1 to 6 carbon ions such methyl ethyl, propyl and hexyl.

The element can comprise one or more additional layers, e.g. separate or combined reagent/spreading layer and a gelatin/buffer layer containing other necessary additives such as electron transfer agents.

The gelatin/buffer layer or the reagent layer or the spreading layer of the element can contain the indicator composition comprising one or more reagents dispersed in one or more synthetic or natural binder materials, such as gelatin, or other naturally-occurring colloids, homopolymers and copolymers, such as poly(acrylamide), poly(vinylpyrrolidone), poly(N-isopropylacrylamide), poly(acrylamide-co-N-vinyl-2-pyrrolidone) and similar copolymers. The indicator composition can also be dispersed in the receptor layer.

Other optional layers, e.g., subbing layers, radiation-blocking layers, etc. can be included if desired. All layers of the element are in fluid contact with each other, meaning that fluids and reagents and uncomplexed reaction products in the fluids can pass between superposed regions of adjacent layers.

The layers of the element can contain a variety of other desirable but optional components, including surfactants, thickeners, buffers, hardeners, antioxidants, coupler solvents, and other materials known in the art. The amounts of these components are also within the skill of a worker in the art.

The elements can be used to determine low concentrations of immunologically reactive ligands in a liquid, such as a biological fluid (e.g., whole blood, serum, plasma, urine, spinal fluid, suspensions of human or animal tissue, feces, saliva, lymphatic fluid and the like). The ligands can be determined at concentrations as low as about $10^{-15}$ molar, and most generally at a concentration of from about $10^{-11}$ to about $10^{-4}$ molar.

Ligands which can be so determined, either quantitatively or qualitatively, include therapeutic drugs (e.g., phenobarbital, digoxin, digitoxin, theophylline, gentamicin, quinidine, phenytoin, propanolol, carbamazepine, tobramycin, lidocaine, procainamide and the like), natural or synthetic steroids (e.g., cortisol, aldosterone, testosterone, progesterone, estriol, etc.), hormones (e.g., thyroid hormones, peptide hormones, insulin, etc.), proteins (e.g. albumin, IgG, IgM, ferritin, blood clotting factors, C-reactive protein, isoenzymes, apolipoproteins, etc.), antigens, antibodies including monoclonal antibodies, and other species which will naturally react with a receptor. This invention is particularly useful for the determination of therapeutic drugs, such as digoxin, phenytoin, theophylline, carbamazepine or phenobarbital and hormones such as thyroxine or triiodothyronine.

The assay can be carried out using any enzyme label which can be attached to the ligand to form a labeled ligand. Enzymes, such as glucose oxidase, peroxidases such as horseradish peroxidase (HRP), amine enriched-horseradish peroxidase (HRP), alkaline phosphatase and galactosidase are preferred labels.

It is within the skill of the ordinary worker in clinical chemistry to determine a suitable substrate for a given label. The substrate can be a material which is directly acted upon by the enzyme label, or a material that is involved in a series of reactions which involve enzymatic reaction of the label. For example, if the enzyme label is a peroxidase, the substrate is hydrogen peroxide plus a suitable reducing agent. Using glucose oxidase as an example, the substrate glucose is generally present in the reagent layer or added as a substrate solution to yield about 0.01 moles/m$^2$, and preferably from about 0.001 to about 0.1 mole/m$^2$. A worker skilled in the art would know how to adjust the amount of a particular substrate for the amount of enzyme label used in the assay.

The reagent layer may contain an indicator composition comprising one or more reagents which provide a detectable species as a result of the reaction catalyzed by the label. The detectable species could develop a color, be radioactive, fluoresce, or be chemiluminescent. For present purposes the invention is illustrated using a colorimetric indicator composition which provides a colorimetrically detectable species as a result of enzymatic reaction of an enzyme-labeled ligand analog with a substrate.

The indicator composition can be a single compound which produces a detectable dye upon enzymatic reaction, or a combination of reagents which produce the dye. For example, when glucose is used as the substrate and glucose oxidase as the enzyme label, the colorimetric indicator composition can include a coupler and an oxidizable compound which react to provide a dye. Alternatively, the composition can include a leuco dye and peroxidase or another suitable peroxidative compound which generates a detectable dye as a result of the formation of hydrogen peroxide produced when glucose oxidase converts glucose to gluconic acid. Useful leuco dyes are known in the art and include those, for example, described in U.S. Pat. No. 4,089,747 (issued May 16, 1978 to Bruschi) and U.S. Ser. No. 612,509, filed May 21, 1984, now U.S. Pat. No. 4,670,385 by Babb et al. The particular amounts of the colorimetric indicator composition and its various components are within the skill of a worker in the art.

The labeled ligands can be prepared using known starting materials and procedures, or obtained commercially. Generally, the ligand is attached to the label (e.g. an enzyme moiety) through a covalent bond.

The immunoassay can be manual or automated. In general, the amount of a ligand in a liquid is determined by taking the element from a supply roll, chip packet or other source and physically contacting a finite area of the spreading layer with a sample of the liquid, e.g. 1 to 100 μL. The finite area which is contacted is generally no more than about 150 mm$^2$.

The amount of ligand is determined by passing the element through a suitable apparatus for detecting the complexed ligand analog directly or the detectable species formed as a result of enzymatic reaction of an enzyme label and a substrate. For example, the species can be detected with suitable spectrophotometric apparatus using generally known procedures. In an enzymatic reaction, the resulting product is determined by measuring, for example, the rate of change of reflection or transmission density in the finite area which was contacted with the test sample. The area which is measured has a diameter of generally from about 3 to about 5 mm. The amount of ligand in the liquid sample is inversely proportional to the amount of label measured in the finite area. Generally, label measurement is made after application of a substrate solution.

The following examples illustrate the practice of this invention.

PREPARATION OF VANADIUM IV CONTAINING POLYMERS

Preparative Example 1

Complex of Vanadyl Sulfate and Poly[acrylamide-co-N-(3-acetoacetamidopropyl)methacrylamide] (Weight Ratio 70/30) (1/1 Polymer/Metal salt).

A 12.5% aqueous solution of poly[acrylamide-co-N-(3-acetoacetamidopropyl)methacrylamide] (weight ratio 70/30) (100 g, 0.017 mol of β-diketone groups) was treated at room temperature with 3.3 g, 0.017 mol of VOSO$_4$.H$_2$O and stirred gently to produce a blue solution ready for use.

Preparative Example 2

Complex of Vanadyl Sulfate and Poly(acrylamide-co-acrylic acid) (Weight Ratio 90/10) (1/1 Polymer/Metal Complex.

A solution of 2.7 g of vanadyl sulfate in 20 mL of water was added to a solution of 10 g (dry) poly(acrylamide-co-acrylic acid) (weight ratio 90/10) in 200 mL of water and stirred gently at room temperature to produce a blue solution of the polymer/metal complex ready for use.

Complexes of vanadyl sulfate were similarly prepared with the following polymers:

| Preparative Example | Polymer | Weight Ratio of Monomers |
|---|---|---|
| 3 | Poly[acrylamide-co-N-(3-acetoacetamidopropyl)-methacrylamide] | 80/20 |
| 4 | Poly[acrylamide-co-N-(3-acetoacetamidopropyl)-methacrylamide] | 90/10 |
| 5 | Poly[acrylamide-co-N-(3-acetoacetamidopropyl)-methacrylamide] | 95/5 |
| 6 | Poly(acrylamide-co-sodium 2-acrylamido-2-methyl-propanesulfonate) | 20/80 |
| 7 | Poly[acrylamide-co-N-t-butylacrylamide-co-N-(3-aminopropyl)methacrylamide hydrochloride] | 45/45/10 |
| 8 | Poly[acrylamide-co-sodium 2-acrylamido-2-methylpropanesulfonate-co-N-(3-acetoacetamidopropyl)methacrylamide] | 50/45/5 |

COMPARATIVE EXAMPLES

Comparative Example 1

An element, free of vanadium IV ($V^{+4}$) containing polymers, for conducting an immunoassay of phenobarbital in serum samples was prepared on a poly(ethylene terephthalate) support. The element had the following configuration and ingredients.

| Layer | Material | Dry Coverage (Grams/Meter$^2$) |
|---|---|---|
| Gravure | Label | $16 \times 10^{-6}$ |
| | Magenta Dye | 0.0269 |
| | MOPS Buffer, pH 7.0 | 0.0045 |
| | BSA | $2.15 \times 10^{-4}$ |
| | Polyacrylamide | $1.08 \times 10^{-3}$ |
| | TX-100 | $4.3 \times 10^{-5}$ |
| | Trehalose | 0.215 |
| Bead Spread Layer | TES Buffer, pH 7.0 | 0.219 |
| | Dimedone | 0.45 |
| | Mannitol | 1.0 |
| | BSA | 1.0 |
| | Glycerol | 2.0 |
| | Adhesive Polymer | 2.58 |
| | Polymer Beads (20–40 uM) | 130.0 |
| Receptor Layer | Polymer Binder | 01.4 |
| | Leuco Dye | 0.20 |
| | Dimedone | 0.05 |
| | Tetronic T908 | 0.02 |
| | Olin 10G | 0.01 |
| | TES Buffer, pH 7.0 | 0.10 |
| | TX-100 | 0.02 |
| | Antibody Beads | 0.10 |
| Gel | Gelatin | 10.0 |
| | 3',5'-dichloro-4'-hydroxyacetanilide | 0.22 |
| | TES Buffer, pH 7.0 | 4.58 |
| | TX-100 | 0.020 |
| | BVSME | 0.150 |

The components listed in the above element and used in subsequent procedures are as follows:

Label: The label was a phenobarbital/amine-enriched horseradish peroxidase conjugate described in example 6 (Label F) prepared as described in U.S. patent applications Ser. No. 851,435, now U.S. Pat. No. 5,284,948, and Ser. No. 851,436, now abandoned, both filed Mar. 16, 1992, and expressly incorporated herein by reference. The label is a conjugate of an amine-enriched amine horseradish peroxidase and a phenobarbital hapten having an extended linking chain.

Magenta Dye: 4,5-Dihydroxy-3-(6,8-disulfo-2-naphthylazo)-2,7-naphthalenedisulfonic acid, sodium salt (KAN 905783).

MOPS: 3-(N-Morpholino)propanesulfonic acid buffer.

BSA: Bovine serum albumin.

TX-100: Triton X-100 surfactant—an octylphenoxy polyethoxy ethanol surfactant sold by Union Carbide.

TES: N-[tris(hydroxymethyl)methyl]-2-aminoethanesulfonic acid buffer.

Adhesive Polymer: Poly(methyl acrylate-co-sodium 2-acrylamido-2-methylpropanesulfonate-co-2-acetoacetoxyethyl methacrylate).

Polymer Beads: Poly(vinyltoluene-co-methacrylic acid) particles having an average diameter in the range of 20–40 µM.

Polymer Binder: Poly(N-isopropylacrylamide-co-2-hydroxyethyl methacrylate-co-N,N'-methylenebisacrylamide).

Leuco Dye: 4,5-Bis(4-dimethylaminophenyl)-2-(3,5-dimethoxy-4-hydroxyphenyl)imidazole.

Tetronic T908: A nonionic surfactant which is a block copolymer of ethylene oxide and propylene oxide sold by BASF Corp.

Olin 10G: An isononylphenoxypolyglycidol surfactant averaging about 10 glycidol units per molecule sold by Olin Chem. Co.

Antibody Beads: Polymer particles of poly[styrene-co-3-(p-vinylbenzythio)propionic acid] having an antibody to carbamazepine covalently bound thereto.

BVSME: Bis(vinylsulfonylmethyl) ether.

DTPA: Diethylenetriaminepentaacetic acid.

Cartridges containing these elements were prepared and placed on a laboratory benchtop overnight. The light in the laboratory was left on overnight. The next day, the elements were tested in a prototype automated thin-film immunoassay analyzer. Ten uL of a test solution Containing 10 ug/mL phenobarbital was applied to an element. The element was then incubated for 5 minutes at 37° C. after which 10 uL of a wash fluid containing $Na_2HPO_4$ (10 mM, pH 6.8), 4'-hydroxyacetanilide (5 mM), hexadecylpyridinium chloride (0.1%), $H_2O_2$(8.8 mM), and DTPA (10 uM) was applied to the slide. This fluid both washes away unbound label from the detection area and initiates the HRP catalyzed color formation reaction. The element was then placed in a 37° C. incubator and reflectance density readings were taken every 3 seconds at 670 nM. The rate of color formation was calculated from these readings. The results were:

| Rate of Top Slide (n = 3)* | Rate on Non-Top Slides (n = 15) | % Rate Loss of Top Slide |
|---|---|---|
| 0.0367 Dt/Min | 0.0725 Dt/Min | −49% |

The top slide had a significantly lower rate than the other slides in the cartridge.

*n=The number of slides tested. The Dt/Min value is the average for the number of slides tested.

Comparative Example 2

The lower rates observed in the top elements could also be induced in elements by removing them from the cartridges and placing them on the benchtop, thereby increasing their exposure to environmental factors (for example, light, air) to which the top elements in cartridges were subjected. This resulted in an even greater loss of rates than observed in the top element in a cartridge.

Phenobarbital elements of the formulation described in comparative Example 1 were placed on a laboratory benchtop overnight. Cartridges containing similar elements were also prepared and also placed on the same laboratory benchtop overnight. The light in the lab was left on during the experiment. The next day, the elements were tested in a prototype automated thin-film immunoassay analyzer as described in comparative Example 1. The results were (the rates from the top elements in cartridges were not included in the data analysis):

| Rate of Benchtop Elements (n = 10) | Rate of Cartridge Elements (n = 15) | % Rate Loss of Benchtop Elements |
|---|---|---|
| 0.0118 Dt/Min | 0.0725 Dt/Min | −84% |

Although this type of exposure was far more severe than encountered by the top element in a cartridge, it provided a convenient experimental system to study the effect of environmental factors on rate of color development.

Comparative Example 3

The improvement in enzyme stability brought about by the polymers of the current invention were evident in another assay using a thin-film coating. In this example, a thin-film of the following formulation was prepared on a poly(ethylene terephthalate) support:

| Layer | Material | Dry Coverage (Grams/Meter$^2$) |
|---|---|---|
| Bead Spread Layer | TES Buffer, pH 7.0 | 0.219 |
|  | Adhesive Polymer | 2.58 |
|  | Polymer Beads (20–40 uM) | 130.0 |
| Receptor Layer | Polymer Binder | 1.4 |
|  | Leuco Dye | 0.20 |
|  | Dimedone | 0.05 |
|  | Tetronic T908 | 0.02 |
|  | Olin 10G | 0.01 |
|  | TES Buffer, pH 7.0 | 0.10 |
|  | TX-100 | 0.02 |
| Gel | Gelatin | 10.0 |
|  | TES Buffer, pH 7.0 | 4.58 |
|  | TX-100 | 0.020 |
|  | BVSME | 0.150 |

This element was used to measure HRP stability with the following protocol. Ten microliters of a solution of 10 mM sodium phosphate buffer, pH 7.0, containing about $3\times10^{-8}$M HRP was spotted onto each of three elements prepared from the thin-film described above. These elements were placed in a dark drawer overnight. The next day, the elements were removed from the drawer and the HRP was extracted by immersing each element in 1 mL of a solution of 10 mM sodium phosphate, 0.15M sodium chloride, 0.1% bovine serum albumin, pH 7.0 in a test tube to extract the HRP. After vortexing the test tube (which removed the thin-film components from the poly(ethylene terephthalate) support), the resulting suspension was centrifuged and the solution removed. The amount of active HRP in this solution was determined by taking a 100 uL aliquot and adding this aliquot to a spectrophotometer cuvette already containing 800 µL of a solution of 10 mM sodium phosphate, pH 6.8, 10 mM diethylenetriaminepentaacetic acid, 5 mM 4'-hydroxyacetanilide, 1.25% polyvinylpyrrolidone, 0.01% 4,5-bis(4-dimethylaminophenyl)-2-(4-hydroxy-3-methoxyphenyl)imidazole leuco dye and 8.8 mM hydrogen peroxide and 100 µL of a solution of 5 mM 4'-hydroxyacetanilide. A blue color was formed whose rate was determined spectrophotometrically at 670 nM. The rate of color formation was directly proportional to the amount of active enzyme in the extract.

In the case described above (the HRP being applied to the element in a solution of 10 mM phosphate buffer, pH 7.0), the amount of active enzyme extracted from the element after the above protocol was followed (fraction active HRP extracted), was compared to the amount of active enzyme applied to the element. The result was:

| HRP Solution | Fraction Active HRP Extracted | % HRP Activity Retained |
|---|---|---|
| Phosphate Buffer | 0.27 | 27% |

EXAMPLES OF THE INVENTION

Examples 1 and 2

The low rate of color formation of the top element would cause the analyte sample tested on this element to be incorrectly predicted. In order to alleviate this situation, the formulation of the elements was improved to prevent environmental factors from having this adverse affect on the top element. It was found that the incorporation of polymers containing vanadium iv in coatings caused the rate of color development in elements placed overnight on the benchtop to be much more resistant to exposure to the environment.

Phenobarbital elements were prepared using the formulation of comparative Example 1 except that the complex of vanadyl sulfate and poly[acrylamide-co-N-(3-acetoacetamidopropyl)methacrylamide] (weight ratio 95/5) of preparative example 5 was incorporated into the bead spread layer at a dry coverage of 0.45 g/m$^2$. In an experiment similar to that described in comparative examples 1 and 2, elements of this new formulation were placed directly on the laboratory benchtop overnight and cartridges containing these new elements were prepared, and the cartridges were also placed on the benchtop overnight. The light in the laboratory was left on overnight. The next day, the elements were tested in a prototype automated thin-film immunoassay analyzer as described in comparative Example 1. The results were (the rates from the top elements in cartridges were not included in the data analysis):

Example 1

Top elements in cartridges were less susceptible to loss of rate when prepared using this new formulation. In an experiment similar to the one described in comparative Example 1 (top element in a cartridge compared to non-top elements in the same cartridge), the results were:

| Rate of Top Element (n = 3) | Rate on Non-Top Elements (n = 15) | % Rate Loss of Top Element |
|---|---|---|
| 0.0540 Dt/Min | 0.0578 Dt/Min | −7% |

In this experiment, the percent rate of the top element compared to the non-top elements (−7%) was improved compared to the original formulation (comparative Example 1, −49%).

Example 2

The new formulation was much better protected even when the elements were left in the open on the bench top.

| Rate of Benchtop Elements (n = 10) | Rate of Cartridge Elements (n = 15) | % Rate Loss of Benchtop Elements |
|---|---|---|
| 0.0338 Dt/Min | 0.0578 Dt/Min | −42% |

The 42% rate loss using the new formulation was much improved compared to the 84% rate loss (comparative Example 2) using the original formulation.

Example 3

The compounds of this invention were added to the solution of HRP and phosphate buffer of Comparative Example 3 so that the concentration of vanadyl ($VO^{+2}$) was 1 mM and the protocol of comparative example 3 was followed. The following results were obtained:

| HRP Solution | Fraction Active HRP Extracted | % HRP Activity Retained |
|---|---|---|
| +Preparative Example 1 | 0.55 | 55% |
| +Preparative Example 3 | 0.57 | 57% |
| +Preparative Example 4 | 0.53 | 53% |
| +Preparative Example 6 | 0.61 | 61% |
| +Preparative Example 7 | 0.61 | 61% |

The percent of HRP activity retained (55–61%) was much improved when these compounds were present compared to a solution containing only phosphate buffer (27%).

Example 4

An element for the assay of thyroxine in serum samples was prepared on a poly(ethylene terephthalate) support. The element was as used in the previous examples except thyroxine antibody beads were used instead of an antibody to phenobarbital. The gravure layer contained no trehalose. The bead spread layer contained a) 0.22 g/m² of 3'5'-dichloro-4'-hydroxyacetanilide; 0.9 g/m² of bovine gamma globulin (BGG) in place of the 1.0 g/m² of BSA; and 0.1 g/m² of tetronic T 908 surfactant. The receptor layer had 0.80 g/m² of polymer binder and the gel layer had 0.44 g/m² of 3,5'-dichloro-4-'hydroxyacetanilide, and 0.165 g/m² of furosemide.

The label in the element was thyroxine horseradish peroxidase. It is a conjugate of horseradish peroxidase and N-[4-(3-(Succinimidoxy-carbonylpropionyl) piperazinocarbonylmethoxyacetyl)]thyr oxine methyl ester prepared according to intermediate preparation 1 and invention preparative example 1 of U.S. patent application Ser. No. 904,614, filed Jun. 26, 1992, and now abandoned, and which is a parent of U.S. Pat. No. 5,527,709 which is expressly incorporated herein by reference.

Coated elements containing polymers of the invention prepared in preparative examples 1, 2, and 3 were incorporated into the bead spread layers of separate elements at a rewet concentration of 2 mM.

| Coating number | Preparative Polymer |
|---|---|
| 1 | 1 |
| 2 | 2 |
| 3 | 3 |

The coatings were cut and mounted as elements. Cartridges containing these elements were prepared and tested as described in comparative example 1 except that 10 mL of a test solution containing 9.2 µg/dL thyroxine was applied to each element. The results were:

| Coating | Rate of Top Element (n = 3) (Dt/min) | Rate of Non-Top Elements (n = 15) (Dt/min) | % Rate Loss of Top Elements |
|---|---|---|---|
| 1 | 0.0705 | 0.0719 | 1.9% |
| 2 | 0.0687 | 0.0713 | 3.6% |
| 3 | 0.0718 | 0.0722 | 1.6% |

There was very little rate loss observed in the top elements of any of these coatings.

The invention has been described in detail with particular reference to preferred embodiments thereof, but it will be understood that variations and modifications can be effected within the spirit and scope of the invention.

We claim:

1. A water soluble polymer containing a) complexed or chelated vanadium IV ions and b) recurring polymerized units having the structure:

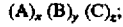

wherein

A represents polymerized hydrophilic monomers selected from the group consisting of acrylamide, N-isopropylacrylamide, N-t-butylacrylamide, 1-vinylimidazole, N-vinylpyrrolidone, N-methylolacrylamide, 2-hydroxyethyl acrylate, and 2,3-dihydroxypropyl acrylate;

B represents polymerized monomers containing an anionic or metal complexing or ligand forming group selected from the group consisting of sulfonate; sulfate; carboxylate; phosphonate; phosphate; β-diketone

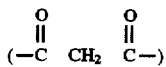

groups; primary, secondary, or tertiary amine groups; carbonyl; carboxy; and hydroxy groups;

C represents recurring units derived from other addition polymerizable monomers which are compatible with an immunoassay analytical element x 20 to 98 weight percent;

y 2 to 80 weight percent; and z 0 to 20 weight percent.

2. The polymer of claim 1 wherein B is a polymerized monomer selected from the group consisting of monomers containing sulfonate, β-diketone or primary amine groups and C represents acrylonitrile, maleimide, methacrylamide or N-t-butylacrylamide.

3. The polymer of claim 1 wherein B represents polymerized N-(3-acetoacetamidopropyl)methacrylamide, 2-acetoacetoxyethyl methacrylate, N-(2-acetoacetoxyethyl)acrylamide, N-(2-acetoacetamidoethyl)methacrylamide, sodium 2-acrylamido-2-methylpropanesulfonate, sodium 3-acryloyloxypropane-1-sulfonate, 2-aminoethyl methacrylate hydrochloride, N-(3-aminopropyl)methacrylamide hydrochloride, acrylic acid, methacrylic acid, 3-(p-vinylbenzylthio)propionic acid, 2-phosphatoethyl acrylate, 2-phosphatoethyl methacrylate, 3-phosphatopropyl acrylate, 3-phosphatopropyl methacrylate, 2-sulfatoethyl methacrylate, or N-(m-& p-vinylbenzyl)nitrilodiacetic acid.

4. The polymer of claim 2 wherein the polymer contains vanadium IV ions and a second polymer selected from the group consisting of poly[acrylamide-co-N-(3-acetoacetamidopropyl)methacrylamide]; poly(acrylamide-co-acrylic acid); poly(acrylamide-co-sodium 2-acrylamido-2-methyl-propanesulfonate); poly[acrylamide-co-N-t-butylacrylamide-co-N-(3 -aminopropyl)methacrylamide hydrochloride]; and poly[acrylamide-co-sodium 2-acrylamido-2-methylpropanesulfonate-co-N-(3-acetoacetamidopropyl)methacrylamide].

5. The polymer of claim 4 wherein the second polymer is selected from the following table:

TABLE

| Polymer Number | Polymer | Weight Ratio of Monomers |
|---|---|---|
| 1 | Poly[acrylamide-co-N-(3-acetoacetamidopropyl)methacrylamide] | 70/30 |
| 2 | Poly(acrylamide-co-acrylic acid) | 90/10 |
| 3 | Poly[acrylamide-co-N-(3-acetoacetamidopropyl)-methacrylamide] | 80/20 |
| 4 | Poly[acrylamide-co-N-(3-acetoacetamidopropyl)-methacrylamide] | 90/10 |
| 5 | Poly[acrylamide-co-N-(3-acetoacetamidopropyl)-methacrylamide] | 95/5 |
| 6 | Poly(acrylamide-co-sodium 2-acrylamido-2-methyl-propanesulfonate) | 20/80 |
| 7 | Poly[acrylamide-co-N-t-butylacrylamide-co-N-(3-aminopropyl)methacrylamide hydrochloride] | 45/45/10 |
| 8 | Poly[acrylamide-co-sodium 2-acrylamido-2-methylpropanesulfonate-co-N-(3-acetoacetamidopropyl)methacrylamide] | 50/45/5 |

* * * * *

UNITED STATES PATENT AND TRADEMARK OFFICE
CERTIFICATE OF CORRECTION

PATENT NO. : 5,696,193
DATED : December 9, 1997
INVENTOR(S) : Daniel S. Daniel, et al.

Page 1 of 2

It is certified that error appears in the above-identified patent and that said Letters Patent is hereby corrected as shown below:

On the title page, item [54], in the title, and column 1:

Line 2, delete "(V+4)" and insert therefor --(V⁻)--.

Column 17, line 1, replace "x 20 to 98 weight percent;" and insert therefor --x is an integer sufficient for (A) to comprise 20 to 98 weight percent of said polymer;--.

Column 17 line 2, replace "y 2 to 80 weight percent; and" and insert therefor --y is an integer sufficient for (B) to comprise 2 to 80 weight percent of said polymer; and--.

Column 17, line 3, replace "z 0 to 20 weight percent." and insert therefor --z is an integer sufficient for (C) to comprise 0 to 20 weight percent of said polymer--.

Column 17, line 22, after "ions and" insert therefor --is present in a composition which also comprises--.

Column 17, line 27, remove space between "butylacrylamine-co-N-(3" and "-aminopropyl)methacrylamide".

UNITED STATES PATENT AND TRADEMARK OFFICE
CERTIFICATE OF CORRECTION

PATENT NO. : 5,696,193

DATED : December 9, 1997

INVENTOR(S) : Daniel S. Daniel, et al.

It is certified that error appears in the above-identified patent and that said Letters Patent is hereby corrected as shown below:

```
        Column 17, line 32, after from, insert
therefor --the group consisting of polymers 1 through
8 in--.
```

Signed and Sealed this

Twenty-fourth Day of March, 1998

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,696,193
DATED : December 9, 1997
INVENTOR(S) : Daniel et al.

It is certified that error appears in the above-identified patent and that said Letters Patent is hereby corrected as shown below:

On the Title Page, Item [54], and column 1, Line 2, delete "VANDIUM" and insert therefor --VANADIUM--.

Column 4, Line 23, replace the current line with the following:

$$(A)_x (B)_y (C)_z;$$

Column 16, Line 44, replace the current line with the following:

$$(A)_x (B)_y (C)_z;$$

Signed and Sealed this

Twenty-seventh Day of February, 2001

*Attest:*

NICHOLAS P. GODICI

*Attesting Officer*     *Acting Director of the United States Patent and Trademark Office*